United States Patent [19]

Hirata et al.

[11] Patent Number: 5,344,809
[45] Date of Patent: Sep. 6, 1994

[54] SYNERGISTIC HERBICIDAL COMPOSITION COMPRISING TRIAZINE HERBICIDES AND AMIDOSULFURON

[75] Inventors: Toshihiro Hirata; Shin-ichiro Ogawa, both of Sodegaura, Japan

[73] Assignee: Idemitsu Kosan Company Limited, Tokyo, Japan

[21] Appl. No.: 70,550

[22] Filed: Jun. 1, 1993

[30] Foreign Application Priority Data

Jun. 8, 1992 [JP] Japan .................................. 4-171530

[51] Int. Cl.$^5$ ........................................... A01N 43/68
[52] U.S. Cl. .................................................. 504/134
[58] Field of Search ........................................ 504/134

[56] References Cited

U.S. PATENT DOCUMENTS

| | | | |
|---|---|---|---|
| 4,601,746 | 7/1986 | Westermann et al. | 71/92 |
| 4,718,937 | 1/1988 | Wilims et al. | 71/93 |
| 4,844,731 | 7/1989 | Takematsu et al. | 71/93 |
| 4,932,998 | 6/1990 | Takematsu et al. | 71/93 |
| 5,169,425 | 12/1992 | Takematsu et al. | 71/88 |
| 5,234,893 | 8/1993 | Hirata et al. | 504/133 |

FOREIGN PATENT DOCUMENTS

| | | |
|---|---|---|
| 0401678 | 12/1990 | European Pat. Off. . |
| 0411153 | 2/1991 | European Pat. Off. . |
| 0467204 | 1/1992 | European Pat. Off. . |
| 0471221 | 2/1992 | European Pat. Off. . |
| 0471284 | 2/1992 | European Pat. Off. . |
| 60-48973 | 3/1985 | Japan . |
| 63-51379 | 3/1988 | Japan . |
| 4-77403 | 3/1992 | Japan . |
| 4-89409 | 3/1992 | Japan . |
| 4-95004 | 3/1992 | Japan . |
| 4-99703 | 3/1992 | Japan . |
| 4-235105 | 8/1992 | Japan . |
| WO90/09378 | 8/1990 | World Int. Prop. O. . |

OTHER PUBLICATIONS

U.S. patent application Ser. No. 07/582,835 filed Oct. 5, 1990.
*The Agrochemicals Handbook,* 3rd ed. "Amidosulfuron", 1991.

*Primary Examiner*—Richard L. Raymond
*Assistant Examiner*—S. Mark Clardy
*Attorney, Agent, or Firm*—Frishauf, Holtz, Goodman & Woodward

[57] ABSTRACT

A herbicidal composition comprising, as active ingredients, a triazine compound of the formula (I):

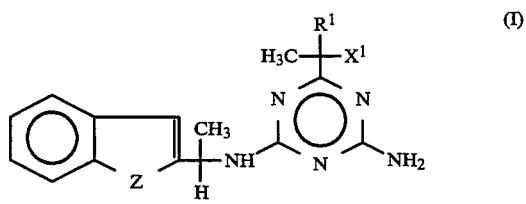

wherein Z is oxygen, sulfur or

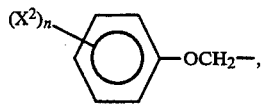

$X^2$ is methyl or fluorine,
n is 0 to 2,
$R^1$ is hydrogen or methyl, and
$X^1$ is fluorine or chlorine,
and a sulfonylurea herbicide of the formula (II):

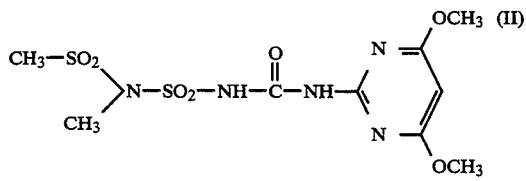

wherein the ratio of the triazine compound to the sulfonylurea herbicide is 100/1 to 1/10 by weight. The herbicidal composition provides a synergistic herbicidal effect against a wide spectrum of weeds, without causing crop injury.

10 Claims, No Drawings

SYNERGISTIC HERBICIDAL COMPOSITION COMPRISING TRIAZINE HERBICIDES AND AMIDOSULFURON

FIELD OF THE INVENTION

The present invention relates to a herbicidal composition comprising a triazine derivative and a particular sulfonylurea herbicide as active ingredients.

BACKGROUND OF THE INVENTION

Heretofore, various herbicides have been developed to contribute toward promoting the agricultural producibility and energy-saving. However, since some herbicides have been used for a long period of time, weeds which could hardly be blighted or exterminated by such herbicides are increasing. Therefore, realization of herbicides having a broader herbicidal spectrum and being effective to even such troublesome weeds is desired. In addition, in order to solve the problem of environmental pollution by conventional herbicides, development of herbicides having a higher activity is also desired. Moreover, in order to control weeds emerging non-uniformly over a long period of time, it has been desired to develop herbicides having excellent residual activities and having flexibility of treatment to exhibit effectiveness, even though the treatment is performed over a long period of time from preemergence to a wide range of growing stage of weeds.

Under the situation, it was already found that particular novel haloalkyl-having triazine derivatives show a high herbicidal effect against troublesome weeds both by soil treatment and by foliage treatment without phytotoxicities of Gramineae crops, and especially that such derivatives show an excellent herbicidal effect against weeds in paddy fields (International Patent Application Laid-Open No. WO 90/09378). The present inventors further made earnest studies so as to improve the herbicidal activity of the triazine derivatives.

SUMMARY OF THE INVENTION

As a result, it has been found that a composition comprising a triazine derivative and a particular sulfonylurea herbicide shows an excellent synergistic herbicidal activity which could not be anticipated from the properties of the individual ingredients and also shows an excellent herbicidal effect of a wide range of herbicidal spectrum even in a low dosage and that the composition is highly safe to crops. On the basis of the findings, the present invention has been completed.

Specifically, the present invention provides a herbicidal composition comprising, as active ingredients, a triazine derivative of a general formula (I):

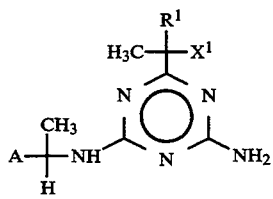

where A represents a group of a formula (a):

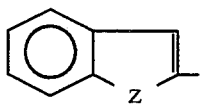

where Z represents an oxygen atom or a sulfur atom, or represents a group of a formula (b):

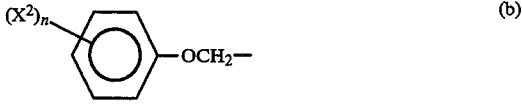

where $X^2$ represents a methyl group or a fluorine atom; and n represents an integer of from 0 to 2;

$R^1$ represents a hydrogen atom or a methyl group; and X represents a fluorine atom or a chlorine atom; and a sulfonylurea herbicide of a formula (II):

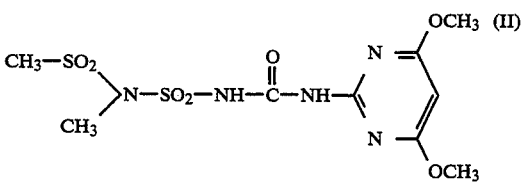

DETAILED DESCRIPTION OF THE INVENTION

The herbicidal composition of the present invention comprises, as active ingredients, a triazine derivative of the above-mentioned general formula (I) and a sulfonylurea herbicide of the above-mentioned formula (II).

Specific examples of triazine derivatives of formula (I) are mentioned below, which, however, are not limitative.

They are 2-amino-4-[1-(benzofuran-2'-yl)ethylamino]-6-($\alpha$-fluoro, $\alpha$-methylethyl)-s-triazine of formula:

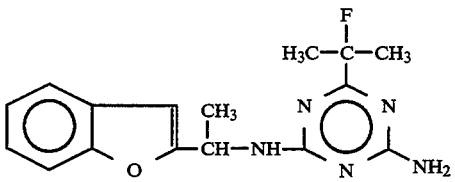

2-amino-4-[1-benzofuran-2'-yl)ethylamino]-6-($\alpha$-fluorethyl)-s-triazine of formula:

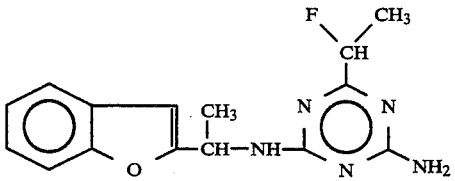

2-amino-4-[1-benzothiophen-2'-yl)ethylamino]-6-($\alpha$-fluoro, $\alpha$-methylethyl)-s-triazine of formula:

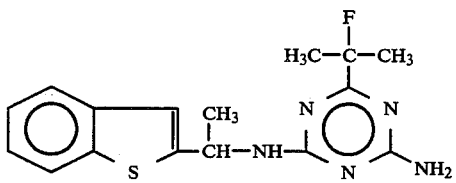

2-amino-4-(α-fluoro, α-methylethyl)-6-[2-(3', 5'-dimethylphenoxy)-1-methyl-ethylamino]-s-trizine of formula:

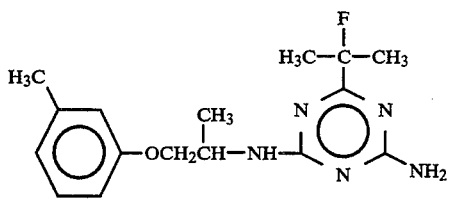

2amino-4(α-fluoro, α-methylethyl)-6-[2-(3'-fluorophenoxy)-1-methylethylamino]-s-triazine of formula:

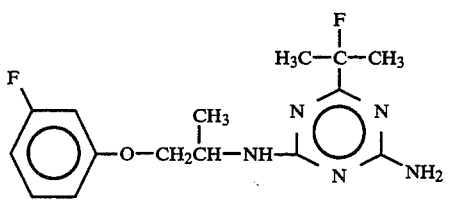

2-amino-4-(α-chloro, α-methylethyl)-6-[2-(3', 5'-dimethylphenoxy)-1-methylethylamino]-s-trizine of formula:

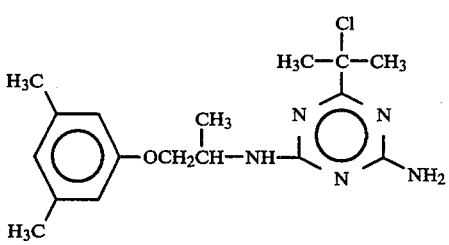

and 2-amino-4(α-fluoro, α-methylethyl)-6-[2-(3', 5'-dimethylphenoxy)-1-methyl-ethylamino]-s-triazine of formula:

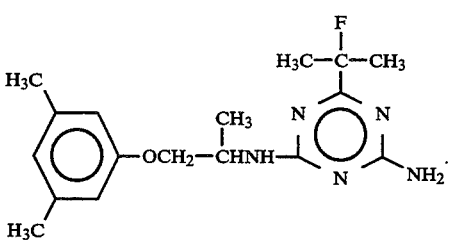

Such triazine derivatives of formula (I) can be produced by various methods. Among these methods, advantageous methods are described in International Patent Application Laid-Open No. WO 90/09378. The disclosure of the laid-open specification is referred to for the details of them.

As mentioned above, the herbicidal composition of the present invention comprises, as active ingredients, a triazine derivative of the above-mentioned general formula (I) and a sulfonylurea herbicide of the above-mentioned formula (II).

The sulfonylurea herbicide of formula (II) is called, as its general name, amidosulfuron and may be obtained by a known method (Japanese Patent Application laid-Open No. 60-48973).

The sulfonylurea herbicide of formula (II) is used in Gramineae crops, such as barley, wheat and oat, but its herbicidal effects against broadleaf weeds such as Veronica hedelifolia, Viola arvensis and the like are insufficient.

The herbicidal composition of the present invention comprises, as active ingredients, a triazine derivative of formula (I) and a sulfonylurea herbicide of formula (II), and the proportion of them is not always specifically defined. The composition shows an excellent synergistic herbicidal effect, having a broadly varying proportion of the ingredients. In general, it is preferred that the ratio of triazine derivative to sulfonylurea herbicide is from 100/1 to 1/10 by weight.

The herbicidal composition of the present invention may be formulated into various forms of wettable powder, emulsifiable concentrate, dust, granules, flowable concentrate, liquid preparation and others for its practical use, by blending a triazine derivative of formula (I) and a sulfonylurea herbicide of formula (II) along with a liquid carrier such as a solvent or with a solid carrier such as a mineral powder. For the formulation, surfactants such as an emulsifier, dispersing agent, spreader, suspending agent, penetrating agent and stabilizer and also other various auxiliary additives may be employed.

Where the herbicidal composition of the present invention is used as a form of a wettable powder, in general, from 10 to 55% by weight of the active ingredients comprising, as mentioned above, a triazine derivative of formula (I) and a sulfonylurea herbicide of formula (II), from 40 to 88% by weight of a solid carrier and from 2 to 5% by weight of a surfactant may be blended and formulated into a wettable powder composition for practical use. If it is used as a form of an emulsifiable concentrate or a flowable concentrate, in general, from 5 to 50% by weight of a mixture of the above-mentioned triazine derivative and sulfonylurea herbicide, from 35 to 90% by weight of a solvent (liquid carrier) and from 5 to 15% by weight of a surfactant and other auxiliary additives may be blended and formulated into a preparation of the desired form.

On the other hand, if it is used as a form of a dust, in general, from 1 to 15% by weight of a mixture of the above-mentioned triazine derivative and sulfonylurea herbicide and from 85 to 99 by weight of a solid carrier may be blended and formulated into a dust.

As the solid carrier, usable is a fine powder of a mineral material. Mineral materials include, for example, oxides such as diatomaceous earth, slaked lime and the like; phosphates such as apatite and the like; sulfates such as gypsum and the like; and silicates such as talc, pyrophyllite, clay, kaolin, bentonire, terra alba, white carbon, quartz powder, silica powder and the like.

As the liquid carrier, usable are organic solvents, including, for example, paraffin or naphthene hydrocarbons such as kerosene, mineral oil, spindle oil and the like; aromatic hydrocarbon such as benzene, toluene, xylene and the like; chlorinated hydrocarbons such as o-chlorotoluene, trichloromethane, trichloroethylene and the like; alcohols such as cyclohexanol, amyl alcohol, ethylene glycol and the like; alcohol ethers such as ethylene glycol monomethyl ether, ethylene glycol monoethyl ether and the like; ketones such as isophorone, cyclohexanone, cyclohexenyl-cyclohexanone and the like; ethers such as butyl cellosolve, dimethyl ether, methyl ethyl ether and the like; esters such as isopropyl acetate, benzyl acetate, methyl phthalate and the like; amides such as dimethylformamide and the like; nitriles such as acetonitrile, propionitrile and the like; sulfoxides such as dimethylsulfoxide and the like; and also water.

As the surfactant, usable is anyone of anionic surfactants (e.g., alkylbenzene sulfonates, alkyl sulfonates, lauric acid amide sulfonates, etc.), nonionic surfactants (e.g., polyoxyethylene octyl ethers, polyethylene glycol laurates, sorbitan alkyl esters, etc.), cationic surfactants (e.g., dimethyllaurylbenzylammonium chloride, laurylamine, stearyltrimethylammonium chloride. etc.) and amphoteric surfactants (e.g., amino acids, betaines, etc.).

The herbicidal composition of the present invention may contain high polymer compounds such as sodium alginate, carboxymethyl cellulose, carboxyvinyl polymer, gum arabi, hydroxypropylmethyl cellulose and the like, and other auxiliary agents, so as to improve its property and to elevate its herbicidal effect.

The herbicidal composition of the present invention can be used for weed control in various field crops, such as wheat, barley, oat and the like, by pre- or post-emergence treatment to the soil or the foliage of weeds, and it shows an excellent herbicidal effect against the weeds as a high-selective herbicide with no crop injury. The herbicidal composition shows a high herbicidal effect not only to annual weeds but also to perennial weeds, and it is also extremely effective for weed control in turf or lawn as a high-selective herbicide with little chemical injury to the growing turf.

In addition, the herbicidal composition of the present invention is also usable for blighting weeds in fruits gardens and various non-agricultural areas (plant zone, railway zone, roads, river-side zone, non-cultivated field, etc.) by pre- or post-emergence treatment to the soil or the foliage of weeds.

In practical use, the herbicidal composition of the present invention is applied in an dosage of from 0. 1 to 2,000 g, preferably from 1 to 200 g, as the active ingredients, per 10 ares. For spraying the composition over the foliage of weeds, the composition is desired to be diluted to have a concentration of from from 1 to 20,000 ppm. preferably from 10 to 2,000 ppm.

The herbicidal composition of the present invention may be combined with any other herbicidal components, if desired. As usable herbicidal components, mentioned are, for example, commercial herbicides such as phenoxyacetic acid compounds, diphenyl ether compounds, triazine compounds, carbamate compounds, thiocarbamate compounds, acid anilide compounds, pyrazole compounds, phosphoric acid compounds, imidazolinone compounds, dinitroaniline compounds, bromoxynil, ioxynil, oxadiazone, etc.

In addition, the herbicidal composition of the present invention may be combined, if desired, with an insecticide, a fungicide, a plant growth regulator, a fertilizer, and others.

The present invention will be explained in more detail by way of the following examples, which, however, are not intended to restrict the scope of the present invention.

First, formulation examples are given, concretely explaining the way of producing herbicidal preparations, in which all "parts" are % by weight. As a triazine derivative (compound A), anyone of compounds (A-1 to A-7) shown in Table 1 below was used; and as a sulfonylurea herbicide (compound B), compound B shown in Table 2 below was used.

TABLE 1

| Compound | Structural Formula | Chemical Name |
| --- | --- | --- |
| A-1 | 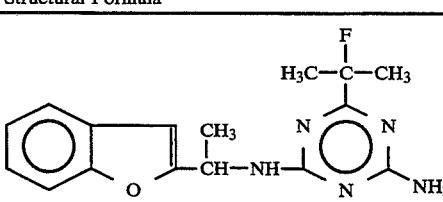 | 2-amino-4-[1-(benzofuran-2'-yl)ethylamino]-6-($\alpha$-fluoro,$\alpha$-methylethyl)-s-triazine |
| A-2 | 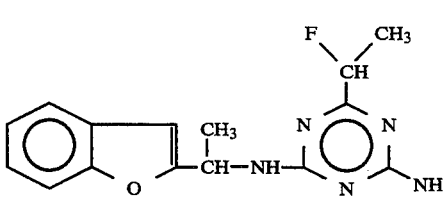 | 2-amino-4-[1-(benzofuran-2'-yl)ethylamino]-6-($\alpha$-fluoroethyl)-s-triazine |
| A-3 | 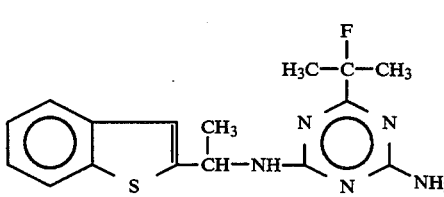 | 2-amino-4-[1-(benzothiophen-2'-yl)ethylamino]-6-($\alpha$-fluoro,$\alpha$-methylethyl)-s-triazine |

TABLE 1-continued

| Compound | Structural Formula | Chemical Name |
|---|---|---|
| A-4 | | 2-amino-4-(α-fluoro,α-methylethyl)-6-[2-(3',5'-dimethylphenoxy)-1-methyl-ehtylamino]-s-triazine |
| A-5 | | 2-amino-4-(α-fluoro,α-methylethyl)-6-[2-(3'-fluorophenoxy)-1-methyl-ethylamino]-s-triazine |
| A-6 | | 2-amino-4-(α-chloro,α-methylethyl)-6-[2-(3',5'-dimethylphenoxy)-1-methylethylamino]-s-triazine |
| A-7 | | 2-amino-4-(α-fluoro,α-methylethyl)-6-[2-(3',5'-dimethylphenoxy)-1-methyl-ethylamino]-s-triazine |

TABLE 2

| Structural Formula of Compound B | Chemical Name |
|---|---|
| | 1-[(N-methylsulfonyl-N-methylamino)-sulfonyl]-3-(4,6-dimethoxy-2-pyrimidinyl)-urea |

| Formulation Example 1: Wettable Powder | |
|---|---|
| Compound A-1 | 5 parts |
| Compound B | 15 parts |
| Diatomaceous Earth | 62 parts |
| White Carbon | 15 parts |
| Sodium Alkylbenzenesulfonate | 2 parts |
| Sodium Ligninsulfonate | 1 part |

The above components are uniformly blended and powdered to prepare a wettable powder of 100 parts.

| Formulation Example 2: Emulsifiable Concentrate | |
|---|---|
| Compound A-2 | 10 parts |
| Compound B | 30 parts |
| Xylene | 20 parts |
| Dimethylformamide | 20 parts |
| Solpol 2806B (surfactant produced by Toho Chemical Industry Co.) | 20 parts |

The above components were uniformly blended and emulsified to prepare an emulsion of 100 parts.

| Formulation Example 3: Dust | |
|---|---|
| Compound A-3 | 0.6 parts |
| Compound B | 1.4 parts |
| Diatomaceous Earth | 20 parts |
| Talc | 78 parts |

The above components were uniformly blended and powdered to prepare a dust of 100 parts.

| Formulation Example 4: Flowable Concentrate | |
|---|---|
| Compound A-7 | 10 parts |
| Compound B | 15 parts |
| Methyl Cellulose | 0.3 parts |
| Colloidal Silica | 1.5 parts |
| Sodium Ligninsulfonate | 1 part |
| Polyoxyethylene Nonyl Phenyl Ether | 2 parts |
| Water | 70.2 parts |

The above components were uniformly blended and dispersed to give a slurry mixture, and this was wet-milled to obtain a stable flowable concentrate of 100 parts.

Formulation Example 5: Wettable Powder 97 parts of clay (JIKURAIRO, trade name by JIKURAIRO KOGYO Co.), as a carrier, 1.5 parts of alkylarylsulfonate (Neopelex, trade name by Kao Atlas Co.) as a surfactant and 1.5 parts of a nonionic and artionic surfactant mixture (Solpol 800A, trade name by Toho Chemical Industry Co.) were uniformly blended and powdered to obtain a carrier blend for wettable powder.

90 parts of the carrier blend was uniformly blended and powdered with 10 parts of anyone of triazine derivatives (A-1 to A-7) shown in Table 1 above or with 10 parts of a sulfonylurea herbicide (compound B) shown in Table 2 above to prepare a wettable powder.

Further, the carrier blend containing triazine derivative obtained above was mixed with the carrier blend containing sulfonylurea herbicide obtained above in a determined proportion of the active ingredients and powdered to prepare a wettable powder.

EXAMPLE 1

Test on Post emergence treatment

Weed seeds of Galium aparine, Veronica hedelifolia and Viola arvensis and crop seeds of wheat, barley and oat were planted each in 1/2000 ares Wagner's pots filled with soil, covered with soil and grown in a greenhouse. A determined amount of the herbicide as obtained in the previous Formulation Example 5 was suspended in water, and the resulting suspension was sprayed uniformly over the foliage of the 1.5-leaves or 2.5-leaves weeds and of the 3-leaves crops at a spray volume corresponding to 100 liters/10 ares. The plants were then grown in the greenhouse. At 20 days after the treatment, the crop injury and the herbicidal effect to the weeds were evaluated in accordance with the following criteria. The results obtained are shown in Tables 3-1 and 3-2 below.

TABLE 3-1

| | | Herbicidal Effect | | | Crop Injury | | |
|---|---|---|---|---|---|---|---|
| Active Ingredient(s) | Dosage (g/10 a) | Galium aparine | Veronica hedelifolia | Viola arvensis | wheat | barley | oat |
| Triazine Derivative A-1 | 10 | 2 | 3 | 3 | 0 | 0 | 0 |
| | 5 | 1 | 2 | 2 | 0 | 0 | 0 |
| Triazine Derivative A-2 | 10 | 3 | 4 | 4 | 0 | 0 | 0 |
| | 5 | 2 | 2 | 3 | 0 | 0 | 0 |
| Triazine Derivative A-3 | 10 | 3 | 3 | 3 | 0 | 0 | 0 |
| | 5 | 1 | 2 | 2 | 0 | 0 | 0 |
| Triazine Derivative A-4 | 10 | 3 | 3 | 4 | 0 | 0 | 0 |
| | 5 | 1 | 2 | 2 | 0 | 0 | 0 |
| Triazine Derivative A-5 | 10 | 3 | 4 | 4 | 0 | 0 | 0 |
| | 5 | 2 | 3 | 3 | 0 | 0 | 0 |
| Triazine Derivative A-6 | 10 | 3 | 3 | 4 | 0 | 0 | 0 |
| | 5 | 1 | 2 | 2 | 0 | 0 | 0 |
| Triazine Derivative A-7 | 10 | 4 | 4 | 4 | 0 | 0 | 0 |
| | 5 | 2 | 2 | 3 | 0 | 0 | 0 |
| Sulfonylurea Herbicide Compound B | 2 | 3 | 2 | 2 | 0 | 0 | 0 |
| | 1 | 1 | 1 | 1 | 0 | 0 | 0 |

TABLE 3-2

| Triazine Derivative | | Sulfonylurea Herbicide | | Herbicidal Effect | | | Crop Injury | | |
|---|---|---|---|---|---|---|---|---|---|
| Compound | Dosage (g/10 a) | Compounds | Dosage (g/10 a) | Galium aparine | Veronica hedelifolia | Viola arvensis | wheat | barley | oat |
| A-1 | 10 | B | 2 | 5 | 5 | 5 | 0 | 0 | 0 |
| | 10 | | 1 | 5 | 5 | 5 | 0 | 0 | 0 |
| | 5 | | 2 | 5 | 5 | 5 | 0 | 0 | 0 |
| | 5 | | 1 | 5 | 5 | 5 | 0 | 0 | 0 |
| A-2 | 10 | B | 2 | 5 | 5 | 5 | 0 | 0 | 0 |
| | 10 | | 1 | 5 | 5 | 5 | 0 | 0 | 0 |
| | 5 | | 2 | 5 | 5 | 5 | 0 | 0 | 0 |
| | 5 | | 1 | 5 | 5 | 5 | 0 | 0 | 0 |
| A-3 | 10 | B | 2 | 5 | 5 | 5 | 0 | 0 | 0 |
| | 10 | | 1 | 5 | 5 | 5 | 0 | 0 | 0 |
| | 5 | | 2 | 5 | 5 | 5 | 0 | 0 | 0 |
| | 5 | | 1 | 5 | 5 | 5 | 0 | 0 | 0 |
| A-4 | 10 | B | 2 | 5 | 5 | 5 | 0 | 0 | 0 |
| | 10 | | 1 | 5 | 5 | 5 | 0 | 0 | 0 |
| | 5 | | 2 | 5 | 5 | 5 | 0 | 0 | 0 |
| | 5 | | 1 | 5 | 5 | 5 | 0 | 0 | 0 |
| A-5 | 10 | B | 2 | 5 | 5 | 5 | 0 | 0 | 0 |
| | 10 | | 1 | 5 | 5 | 5 | 0 | 0 | 0 |
| | 5 | | 2 | 5 | 5 | 5 | 0 | 0 | 0 |
| | 5 | | 1 | 5 | 5 | 5 | 0 | 0 | 0 |
| A-6 | 10 | B | 2 | 5 | 5 | 5 | 0 | 0 | 0 |

TABLE 3-2-continued

| Triazine Derivative | | Sulfonylurea Herbicide | | Herbicidal Effect | | | Crop Injury | | |
|---|---|---|---|---|---|---|---|---|---|
| Compound | Dosage (g/10 a) | Compounds | Dosage (g/10 a) | Galium aparine | Veronica hedelifolia | Viola arvensis | wheat | barley | oat |
| | 10 | | 1 | 5 | 5 | 5 | 0 | 0 | 0 |
| | 5 | | 2 | 5 | 5 | 5 | 0 | 0 | 0 |
| | 5 | | 1 | 5 | 5 | 5 | 0 | 0 | 0 |
| A-7 | 10 | B | 2 | 5 | 5 | 5 | 0 | 0 | 0 |
| | 10 | | 1 | 5 | 5 | 5 | 0 | 0 | 0 |
| | 5 | | 2 | 5 | 5 | 5 | 0 | 0 | 0 |
| | 5 | | 1 | 5 | 5 | 5 | 0 | 0 | 0 |

The criteria for evaluation of the herbicidal effects in Tables 3-1 and 3-2 above are as follows:

| Degree of Herbicidal Effect | Herbicidal Rate (percentage of weed control) |
|---|---|
| 0 | less than 5% (almost ineffective) |
| 1 | 5 to 20% |
| 2 | 20 to 40% |
| 3 | 40 to 70% |
| 4 | 70 to 90% |
| 5 | more than 90% (almost completely killed) |

The herbicidal rate (percentage of weed control) was determined according to the following equation, after measuring the weight of the on-the-ground parts in the treated group and that in the non-treated group.

Herbicidal effect (%)

= [1- (weight of on-the-ground parts in treated group)/(weight of on-the-ground parts in non-treated group)] × 100

The crop injury in Tables 3-1 and 3-2 above was determined in accordance with the following 6-rank criteria:

Degree of Crop Injury:

0: No injury to crops was observed.
1: Almost no injury to crops was observed.
2: Some injury to crops was observed.
3: Injury to crops was observed.
4: Serious injury to crops was observed.
5: Almost crops were killed.

Some data were picked up from Tables 3-1 and 3-2 above, and the synergistic herbicidal effect of the respective compositions comprising the triazine derivative and the sulfonylurea herbicide was examined against weeds of Oalium aparine and Viola arvensis. Concretely, the effect was evaluated from the estimated value QE as obtained from the following equation.

$QE = Qa + Qb - (Qa \cdot Qb/100)$ where Qa indicates the herbicidal rate (%), when the active ingredient of only the triazine derivative was used for the treatment in an amount of a g/10 ares; Qb indicates the herbicidal rate (%), when the active ingredient of only the sulfonylurea herbicide was used for the treatment in an amount of b g/10 ares; and QE indicates the estimated value.

For the calculation, L.E. Limpel, P.H. Schuldt and D. Lamont. Proc. NEWCC. 16, 48-53 (1962) was referred to.

If the herbicidal rate (percentage of weed control) of the composition comprising the triazine derivative and the sulfonylurea herbicide is larger than QE (estimated value), it is concluded that the synergistic herbicidal effect of the composition was attained. The results obtained are shown in Table 4 below.

TABLE 4

| Active Ingredient(s) | Dosage (g/10 a) | Herbicidal rate (%) to Galium aparine | Estimated Value ($Q_E$) (%) | Herbicidal rate (%) to Viola arvensis | Estimated Value ($Q_E$) (%) |
|---|---|---|---|---|---|
| A-1 + B | 10 + 2 | 94 | 67 | 96 | 63 |
| | 10 + 1 | 92 | 49 | 94 | 55 |
| A-2 + B | 5 + 2 | 98 | 65 | 98 | 74 |
| | 5 + 1 | 93 | 48 | 96 | 68 |
| A-3 + B | 10 + 2 | 97 | 74 | 98 | 69 |
| | 10 + 1 | 95 | 61 | 97 | 61 |
| A-4 + B | 10 + 2 | 96 | 75 | 97 | 77 |
| | 10 + 1 | 92 | 63 | 95 | 71 |
| A-5 + B | 5 + 2 | 94 | 65 | 98 | 76 |
| | 5 + 1 | 93 | 48 | 93 | 70 |
| A-6 + B | 10 + 2 | 98 | 79 | 96 | 80 |
| | 10 + 1 | 97 | 69 | 95 | 75 |
| A-7 + B | 5 + 2 | 98 | 68 | 98 | 70 |
| | 5 + 1 | 96 | 51 | 97 | 63 |
| A-1 | 10 | 38 | — | 46 | — |
| A-2 | 5 | 36 | — | 62 | — |
| A-3 | 10 | 52 | — | 54 | — |
| A-4 | 10 | 54 | — | 66 | — |
| A-5 | 5 | 36 | — | 64 | — |
| A-6 | 10 | 62 | — | 70 | — |
| A-7 | 5 | 40 | — | 56 | — |
| B | 2 | 46 | — | 32 | — |
| | 1 | 18 | — | 16 | — |

EXAMPLE 2

Field Test (Post emergence treatment test)

Test fields each having an area of 2 m2 were prepared, and weed seeds of Galium aparine, Stellaria media, Viola arvensis, Matricaria inodora and Veronica hedelifolia and crop seeds of wheat and barley were planted at the same time.

When the weeds grew up to 2-3 leaves stage and when wheat and barley grew up to 3-leaves stage, a determined amount of the dilution of the herbicidal composition obtained in the previous Formulation Example 5 was uniformly sprayed over the foliage of the weeds and the crops at a spray volume corresponding to 20 liters/10 ares.

30 days after the treatment, the on-the-ground parts of weeds were cut out and the weight of them was measured. The herbicidal rate (percentage of weed control) of the composition was obtained [rom the following equation, as the average of the three test plots. The weight of the on-the-ground parts of wheat or barley were also measured in the same manner, and the crop injury to them (percentage of crop injury) of the composition was also obtained in the same manner. The results are shown in Table 5 below.

Herbicidal rate (percentage of weed control) (%)

=[1-(weight of living weeds in treated test plot)/(weight of living weeds in the non-treated plot)]=100

TABLE 5

| Active Ingredients | Dosage (g/10 a) | Herbicidal Rate (percentage of weed control) | | | | | Crop Injury | |
|---|---|---|---|---|---|---|---|---|
| | | Galium aparine | Stellaria media | Viola arvensis | Matricaria inodora | Veronica hedelifolia | wheat | barley |
| A-2 + B | 20 + 3 | 100 | 100 | 100 | 100 | 100 | 0 | 0 |
| | 10 + 3 | 100 | 100 | 100 | 100 | 100 | 0 | 0 |
| A-7 + B | 20 + 3 | 100 | 100 | 100 | 100 | 100 | 0 | 0 |
| | 10 + 3 | 100 | 100 | 100 | 100 | 100 | 0 | 0 |

As explained in detail in the above description, the herbicidal composition of the present invention shows a high herbicidal effect even when used in a low dosage, because of the synergistic effect of the active ingredients of the triazine derivative and the sulfonylurea herbicide, and it has a wide range of herbicidal spectrum.

In addition, the herbicidal composition of the present invention shows an excellent activity even to troublesome weeds.

Further, the herbicidal composition of the present invention is highly safe to crop plants without causing any crop injury to them.

While the invention has been described in detail and with reference to specific embodiments thereof, it will be apparent to one skilled in the art that various changes and modifications can be made therein without departing from the spirit and scope thereof.

What is claimed is:

1. A herbicidal composition comprising, as active ingredients, a triazine compound of a formula (I):

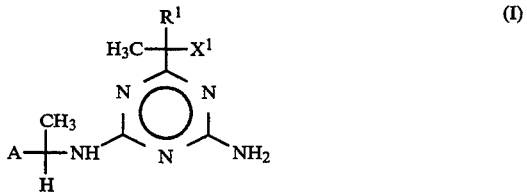

where A represents a group of a formula (a):

where Z represents an oxygen atom or a sulfur atom, or represents a group of a formula (b):

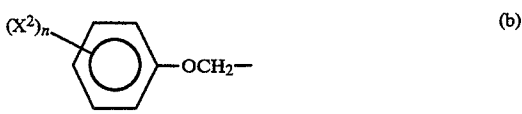

where $X^2$ represents a methyl group or a fluorine atom; and n represents an integer of from 0 to 2;

$R^1$ represents a hydrogen atom or a methyl group; and $X^1$ represents a fluorine atom or a chlorine atom; and a sulfonylurea herbicide of a formula (II):

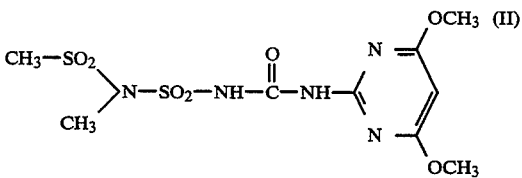

wherein the weight ratio of said triazine compound to the sulfonylurea herbicide is 100/1 to 1/10 by weight.

2. The herbicidal composition as claimed in claim 1, wherein the triazine compound is 2-amino-4-[1-(benzofuran-2'-yl)ethylamino]-6-(α-fluoro, α-methylethyl)-s-triazine.

3. The herbicidal composition as claimed in claim 1, wherein the triazine compound is 2-amino-4-[1-(benzofuran-2'-yl)ethylamino]-6-(α-fluoroethyl)-s-triazine.

4. The herbicidal composition as claimed in claim 1, wherein the triazine compound is 2-amino-4-[1-(benzothiopen-2'-yl)ethylamino]-6-(α-fluoro, α-methylethyl)-s-triazine.

5. The herbicidal composition as claimed in claim 1, wherein the triazine compound is 2-amino-4-(α-fluoro, α-methylethyl)-6-[2-(3', 5'-dimethylphenoxy)-1-methylethylamino]-s-triazine.

6. The herbicidal composition as claimed in claim 1, wherein the triazine compound is 2-amino-4-(α-fluoro, α-methylethyl)-6-[2-(3'-fluorophenoxy-1-methylethylamino]-s-triazine.

7. The herbicidal composition as claimed in claim 1, wherein the triazine compound is 2-amino-4-(α-chloro, α-methylethyl)-6-[2-(3', 5'-dimethylphenoxy)-1-methylethylamino]-s-triazine.

8. The herbicidal composition as claimed in claim 1, wherein the triazine compound is 2-amino-4-(α-fluoro, α-methylethyl)-6-[2-(3', 5'-dimethylphenoxy)-1-methylethylamino]-s-triazine.

9. A method of combating weeds comprising applying to weeds or to a locus thereof an effective herbicidal amount of the herbicidal composition according to claim 1.

10. The method as claimed in claim 9, wherein the triazine compound is selected from the group consisting of 2-amino-4-[1-(benzofuran-2'-yl) ethylamino]-6-(α-fluoro, α-methylethyl)-s-triazine, 2-amino-4-[1-(benzofuran-2'-yl)ethylamino]-6-(α-fluorethyl)-s-triazine, 2-amino-4-[1-benzothiopen-2'-yl)ethylamino]-6-(α-fluoro, α-methylethyl)-s-triazine, 2-amino-4-(α-fluoro, α-methylethyl)-6-[2-(3', 5'-dimethylphenoxy)-1-methylethylamino]-s-triazine, 2-amino-4-(α-fluoro, α-methylethyl)-6-[2-(3'-fluorophenoxy)-1-methylethylamino]-s-triazine, 2-amino-4-(α-chloro, α-methylethyl)-6-[2-(3', 5'-dimethylphenoxy)-1-methylethylamino]-2-triazine, and 2-amino-4-(α-fluoro, α-methylethyl)-6-[2-(3', 5'-dimethylphenoxy)-1-methylethylamino]-s-triazine.

* * * * *